(12) United States Patent
Chao

(10) Patent No.: US 7,659,510 B2
(45) Date of Patent: Feb. 9, 2010

(54) CRYO-CHARGING SPECIMEN HOLDER FOR ELECTRON MICROSCOPE

(76) Inventor: Chih-Yu Chao, Department of Physics, National Taiwan University, No. 1, Sec. 4, Roosevelt Road, Taipei (TW) 106

( * ) Notice: Subject to any disclaimer, the term of this patent is extended or adjusted under 35 U.S.C. 154(b) by 193 days.

(21) Appl. No.: 12/078,223

(22) Filed: Mar. 28, 2008

(65) Prior Publication Data

US 2009/0242795 A1   Oct. 1, 2009

(51) Int. Cl.
*H01J 49/44* (2006.01)
(52) U.S. Cl. ..................................... 250/311
(58) Field of Classification Search ............... 250/311, 250/306, 307, 310
See application file for complete search history.

(56) References Cited

U.S. PATENT DOCUMENTS 6,875,984 B2 *  4/2005  Kakibayashi et al. ....... 250/311
7,413,872 B2 *  8/2008  Frederik et al. ............... 435/67
7,420,184 B2 *  9/2008  van de Water et al. ... 250/442.11

OTHER PUBLICATIONS

Chao, Chih-Yu; Bio-Molecular Microscopy at Atomic Resolution, Chinese Journal of Physics, Dec. 2007, vol. 45, No. 6-I, pp. 557-578, The Physical Society of the Republic of China.

* cited by examiner

*Primary Examiner*—Kiet T Nguyen
(74) *Attorney, Agent, or Firm*—Bacon & Thomas, PLLC

(57) ABSTRACT

The present invention relates to a cryo-charging specimen holder for the electron microscope, particularly to a cryo-charging specimen holder for the electron microscope to hold various biological materials. The major feature of the invention is to charge the biological specimen and freeze the specimen at low temperature. The ice around the biological sample is also doped, so that after charging the doped ice surrounding the sample has a conductivity level comparable to that of conductor. Therefore, the sample can be embedded by the doped and charged ice obtaining the property of conductor, in order to be observed by the electron microscope.

12 Claims, 14 Drawing Sheets

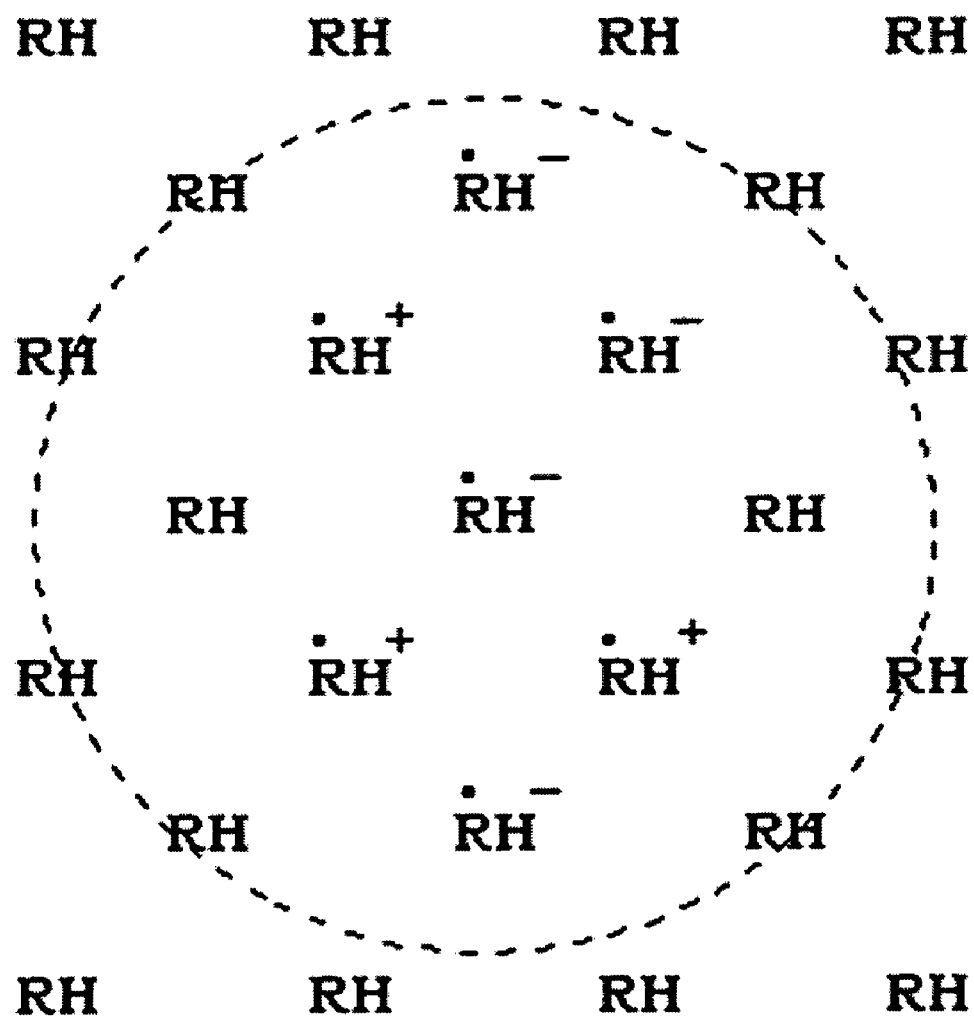
Figure 7A1

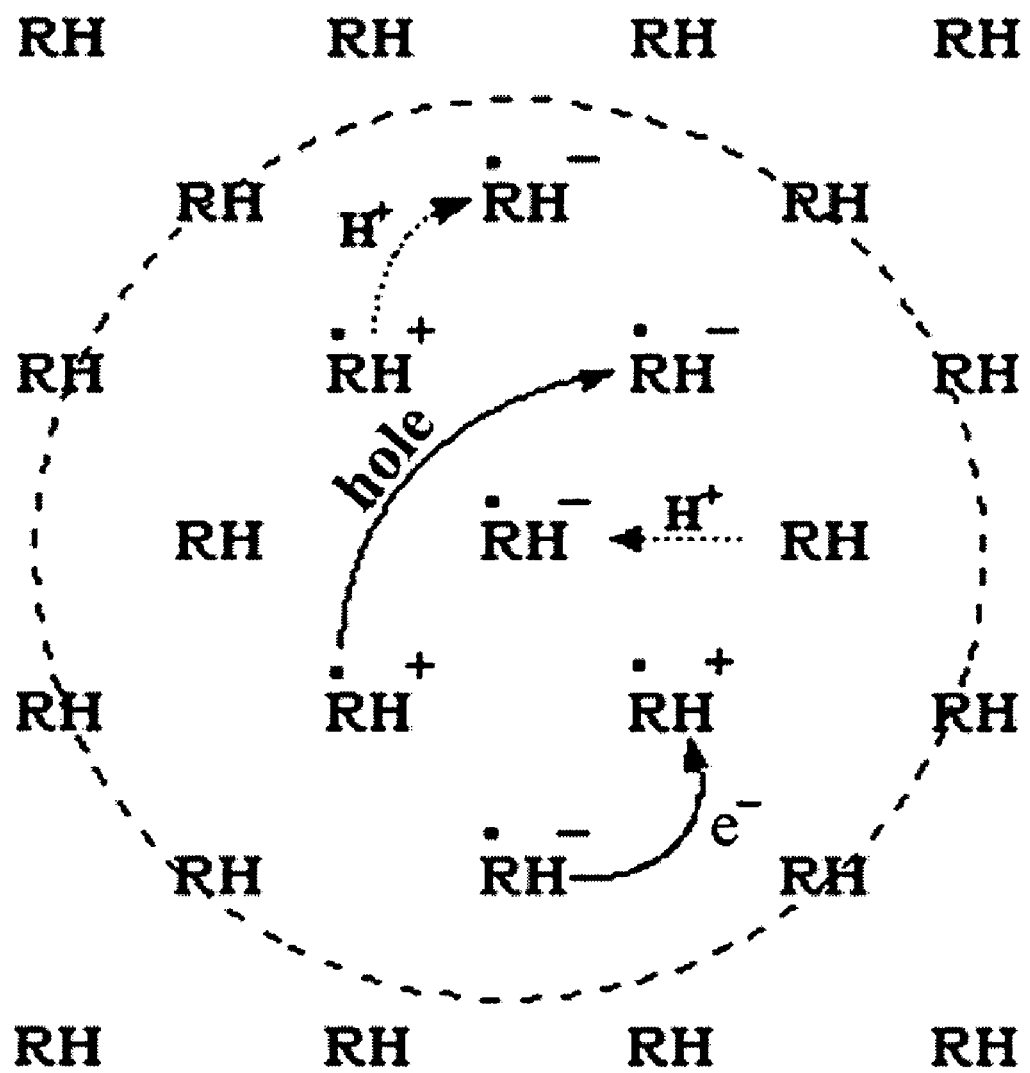
Figure 7A2

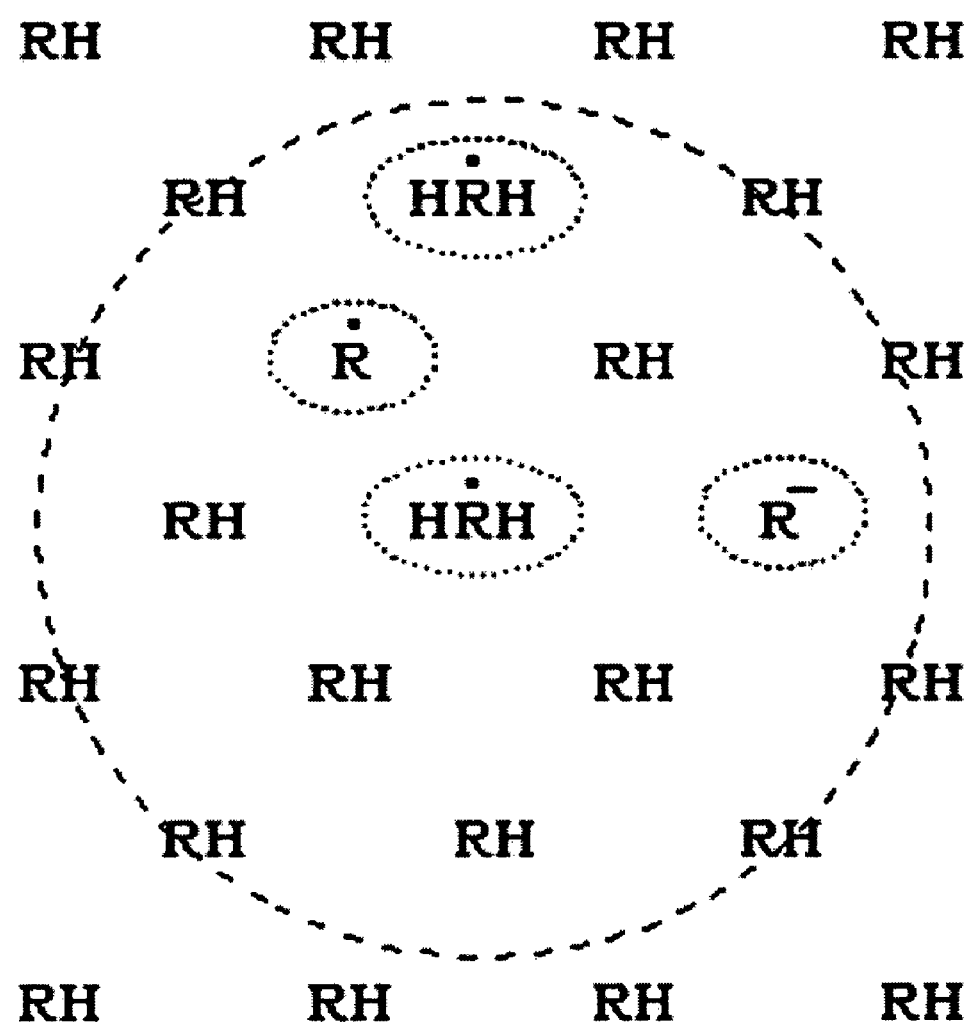
Figure 7A3

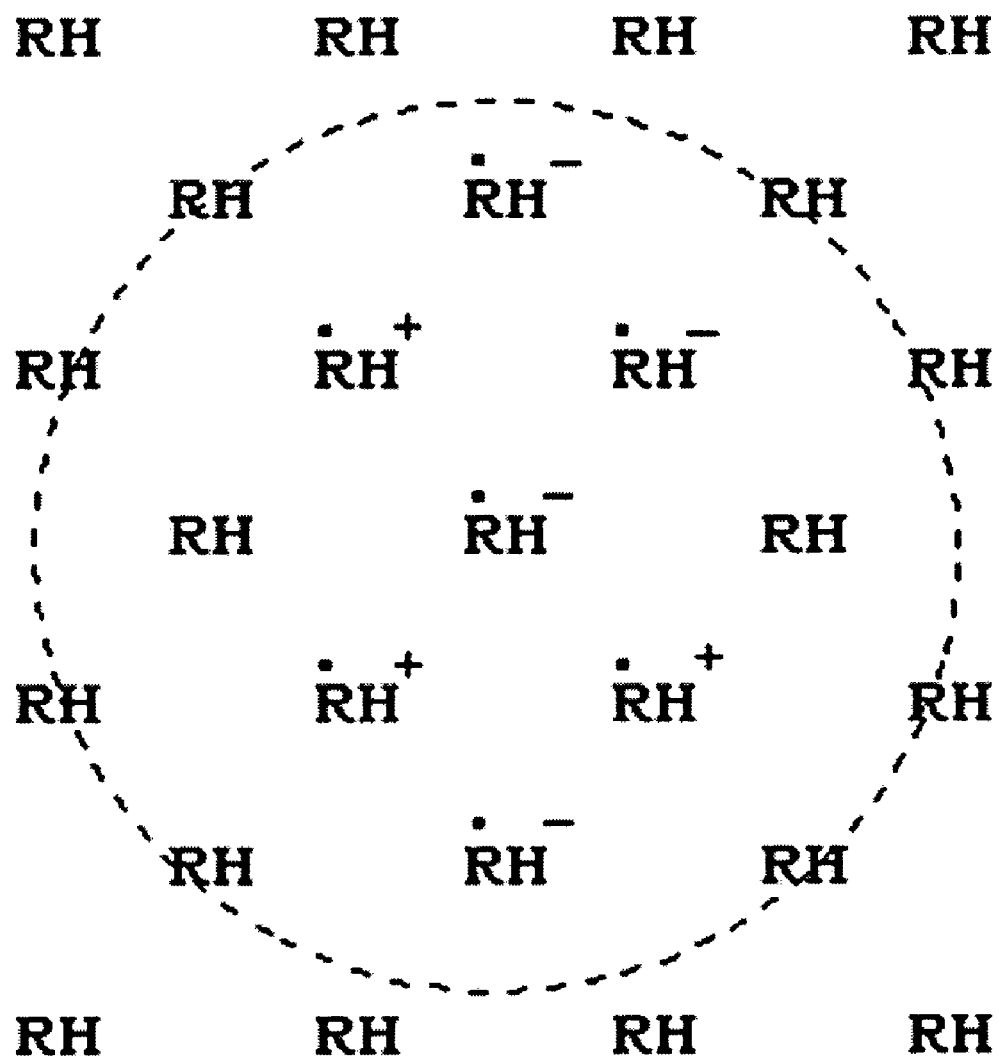
Figure 7B1

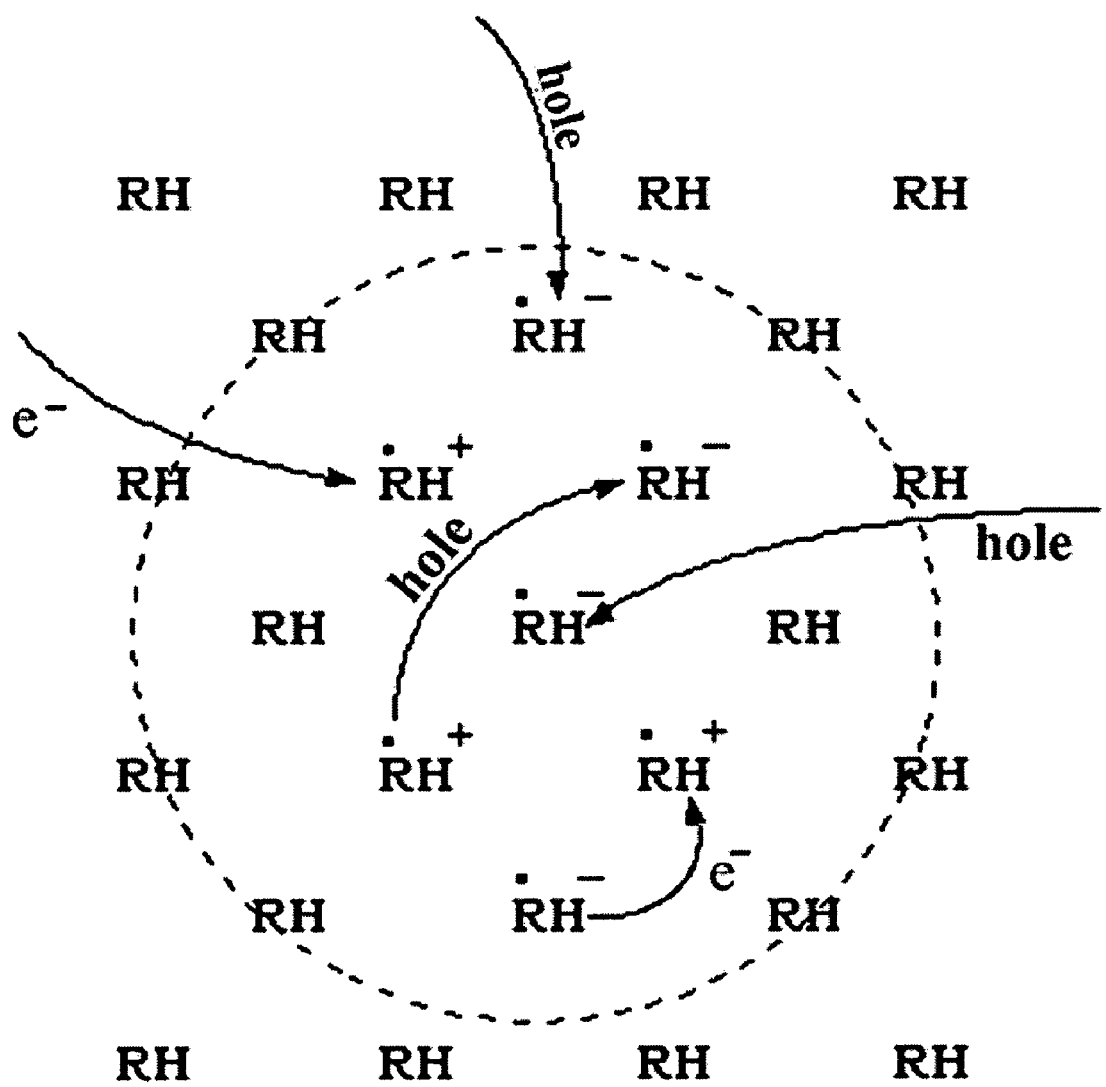
Figure 7B2

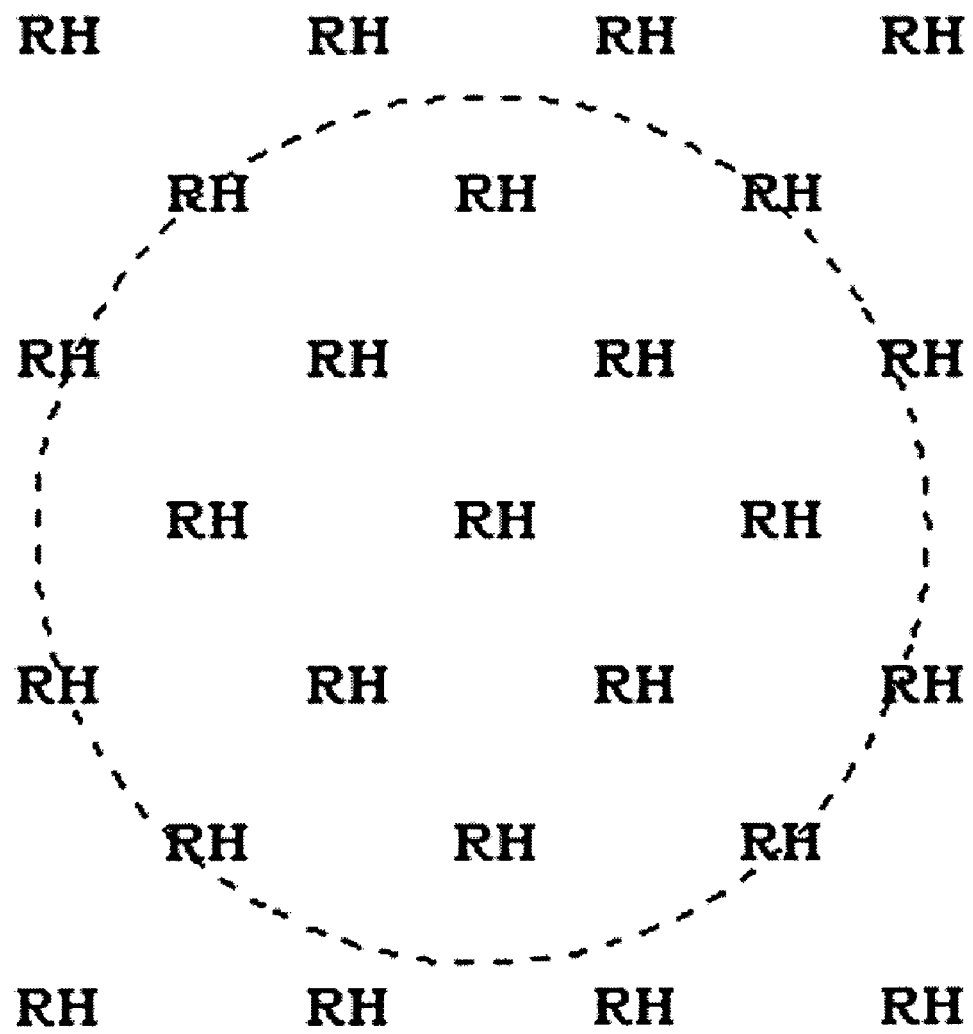
Figure 7B3

CRYO-CHARGING SPECIMEN HOLDER FOR ELECTRON MICROSCOPE

BACKGROUND OF THE INVENTION

1. Field of the Invention

The present invention relates to a cryo-charging specimen holder for the electron microscope, and more particularly, to a cryo-charging specimen holder for the electron microscope to hold various biological materials.

2. Description of the Prior Art

At present, the knowledge of the mankind have already tried to enter the post gene era, but unfortunately, only can understand less than 0.5% of the protein structure. For the analysis of protein structure, especially the analysis for the nano-scale biological molecular structure is very important on the disease prevention, gene replication and renovation etc.

In the prior art, the primary tools for determining protein structure are the x-ray diffraction (XRD) and the Nuclear Magnetic Resonance (NMR) techniques. Nevertheless, the structures of only a small number of macromolecular complexes and proteins have been successfully determined by using XRD, comprising only a tiny portion of the protein data bank. In fact, not all proteins can be crystallized for XRD measurements. Crystallization of protein remains a major hurdle, and to date 99.5% of proteins are difficult to be formed as crystal. Moreover, the crystallization for every kind of protein is a highly difficult process, and process may somehow damage the native form of protein. On the other hand, the conventional NMR technique is only suitable for the observation of small molecules, not generally applicable to all macromolecular complexes and proteins.

In addition, the cryo-electron microscopy can be used to observe protein structure. In the cryo-electron microscopy, the proteins do not need to be crystallized. Rather, the biological specimens are prepared by rapid freezing the samples. Then, the samples are embedded in amorphous ice to form as observable specimens. There are many advantages for the cryo-electron microscopy compared to the above-mentioned XRD and NMR techniques. However, the cryo-electron microscopy is not able to provide the atomic resolution. The main reason is that the dosage of electron radiation must be restricted to 10-20 e/Å$^2$ in the cryo-electron microscopy. It means excess electron dosage will damage the biological materials. The movement of damaged molecular fragments caused by electron radiation can blur the image anisotropically in a relatively unpredictable manner, preventing the atomic resolution from being obtained. Therefore, the cryo-electron microscopy is not well practicable.

Thus, after the mankind enters the post gene era, in order to understand the structure and function for more proteins, it is necessary to develop the bio-molecular microscope with the atomic-level resolution, and promote the development and advancement of natural science field through the observation of biological materials and proteins etc. via the improvement of the technical tools.

SUMMARY OF THE INVENTION

The present invention relates to a cryo-charging specimen holder for the electron microscope, particularly to a cryo-charging specimen holder of electron microscope to hold various biological materials.

The major feature of the invention is to charge the biological specimen and freeze the specimen at low temperature. The ice around the biological sample is also doped, so that after charging the doped ice surrounding the sample has a conductivity level comparable to that of conductor. Thus, the sample can be embedded by the doped and charged ice obtaining the property of conductor, in order to be observed by the electron microscope.

In the present invention, the cryo-charging specimen holder of electron microscope mainly comprises the following elements:

A power supply is connected to the resistor via the electrical wires and connected to the specimen holder through the specimen rod. A vacuum adiabatic flask having an inner pot is provided, wherein a vacuum space is located between the vacuum adiabatic flask and the inner pot. A low-temperature liquefied medium such as liquid nitrogen or liquid helium is filled into the inner pot to be used as liquid cooling medium. The vacuum adiabatic flask is connected to the specimen rod.

The present invention relates to a method to use the cryo-charging specimen holder for the electron microscope, which comprises the following steps:

Firstly, the vacuum treatment is conducted. And low temperature is conducted to the specimen holder through the specimen rod to carry on the low-temperature treatment. Next, the specimen grid is loaded on the specimen holder, where the biological specimen has been loaded in the specimen grid. Then, the cryo-charging specimen holder is put into the electron microscope. And the suitable current is provided to charge the biological specimen. Finally, the biological specimen is observed by the electron microscope.

The invention can greatly reduce the radiation damage of biological samples during the electron beam irradiation. Thus, the native form of biological materials can be observed clearly.

The invention can break through the key technology of the electron microscope, so that the bio-molecular microscope with atomic-level resolution can be developed successfully.

The invention can raise the resolution of the electron microscope by the way of saving cost. And only the key technology has to be developed, then the resolution of any electron microscope can be raised.

There are many important advantages for the invention, and also the fabrication of elements is not difficult, thus different proteins can be observed, which can be applied in the relevant fields of biology, physics, medicine, and bio-chemistry etc.

In addition, the advantages and spirits of the invention will become apparent from the following detailed description in conjunction with the accompanying drawings.

BRIEF DESCRIPTION OF THE DRAWINGS

FIG. 7A1, 7A2, 7A3 and FIG. 7B1, 7B2, 7B3 are the diagrams schematically illustrating the damaged molecular fragments of frozen hydrated DNA caused by electron beam irradiation and the transfer of the electron and hole inside and outside the DNA cluster of the invention.

DESCRIPTION OF THE PREFERRED EMBODIMENT

The invention will be understood sufficiently through the description of the following embodiments, and those skilled in the art can complete it accordingly. However, the implementation will not be limited by the following embodiments.

The present invention relates to a cryo-charging specimen holder for the electron microscope, particularly to a cryo-charging specimen holder for the electron microscope to hold various biological materials, which is suitable to be used by various electron microscopes directly. After the cryo-charging specimen holder for the electron microscope of this invention is installed, the electron microscope can become the bio-molecular microscope with atomic resolution directly without any modification.

Figure 1:
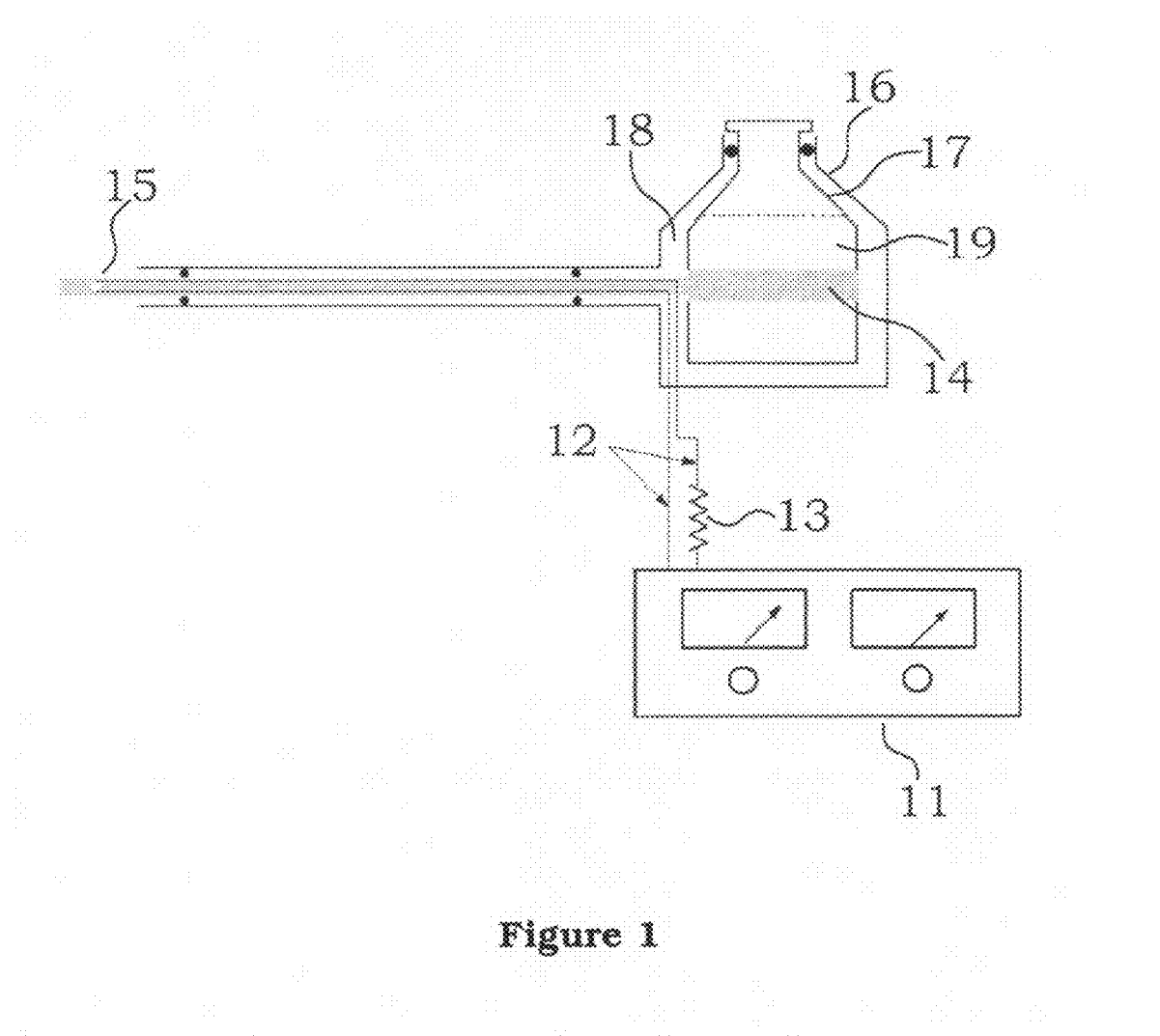
FIG. 1 is the diagram schematically illustrating the preferred embodiment of the invention.

Please refer to FIG. 1, which shows the schematic of cryo-charging specimen holder of electron microscope of this invention and comprises the following elements:

Thus, in the embodiment shown in FIG. 1, the elements of cryo-charging specimen holder of electron microscope are described as follows:

A power supply 11 is connected to the resistor 13 via the electrical wires 12 and connected to the specimen holder 15 through the specimen rod 14.

A vacuum adiabatic flask 16 (such as conventional Dewar flask) having inner pot 17 is provided, wherein a vacuum space 18 is located between the vacuum adiabatic flask 16 and the inner pot 17. A low-temperature liquefied medium 19 such as liquid nitrogen or liquid helium is filled into the inner pot 17 to be used as liquid cooling medium 19. The inner pot 17 is connected to the specimen rod 14. Both of the inner pot 17 and the specimen rod 14 shall contact directly, so that the low temperature of liquid cooling medium 19 can be transferred from the specimen rod 14 to the specimen holder 15.

Figure 2:
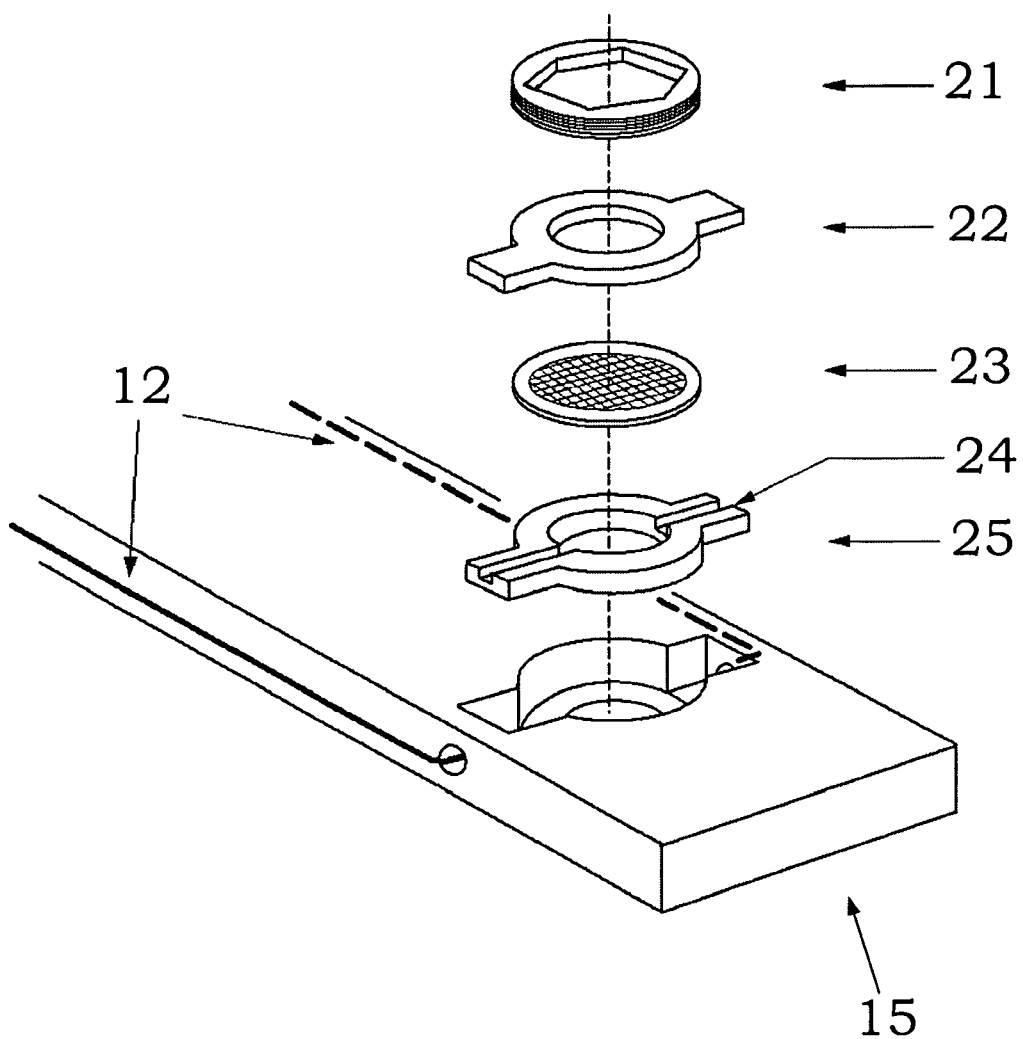
FIG. 2 is the exploded diagram schematically illustrating the preferred embodiment of the invention.

As shown in FIG. 2, the exploded diagram of the specimen holder 15 shown in FIG. 1 is amplified, wherein the elements are:

Hexring screw 21, the function for Hexring screw 21 is defined as fixing function.

Teflon washer 22, the function for Teflon washer 22 is defined as fixing and insulation function.

Specimen grid 23, the function for Specimen grid 23 is defined as specimen loading function.

Groove for electrical wire 24, the function for Groove for electrical wire 24 is defined as electrical wire passage function.

Teflon washer 25, the function for Teflon washer 25 is defined as fixing and insulation function.

In the preferred embodiment shown in FIG. 2, after the pretreated specimen grid 23 is put into the specimen holder 15, the Teflon washers 22 and 25 are used to fix and insulate the specimen grid 23. The electrical wires 12 are passed through the groove 24 to the specimen. Then, the Hexring screw 21 is used to lock two Teflon washers, thus the electrical wires 12 can make a good contact with the specimen grid 23.

In the preferred embodiment of the cryo-charging specimen holder for the electron microscope shown in FIG. 1, the operation way is shown as the followings:

Firstly, the specimen holder shall be vacuumed.

Next, the liquid cooling medium 19 such as liquid nitrogen or liquid helium is filled into the inner pot 17 to be used as liquid cooling medium 19. It is transferred from the specimen rod 14 to the specimen holder 15 for low-temperature treatment.

Next, installing the pretreated specimen grid 23 is carried out, which means to put the specimen grid 23 having the biological material into the specimen holder 15 and fix up.

Then, installing the specimen holder 15 in the electron microscope is achieved.

Continually, using power supply 11 to provide suitable current to charging the specimen through the resistor 13 connected to electrical wires 12.

Finally, observing and photographing by the electron microscope both are carried out.

In the embodiment, the pretreated process of the invention will comprise:

Putting the biological molecule into sodium chloride aqueous solution, which means to put the biological materials such as protein etc. into sodium chloride (NaCl) aqueous solution with suitable concentration. The concentration of sodium chloride aqueous solution is between 1 μM to 100 mM. After the sodium ion is doped into the aqueous solution, the solution can provide a conduction channel close to the Fermi level. This conduction channel is also called the lowest unoccupied molecular orbital (LUMO).

Next, the sodium chloride aqueous solution having the biological molecule is dropped into the specimen grid 23.

Then, the filter paper will be used to removing excess solution. Low-temperature liquid ethane is used to freeze the specimen grid to 77K rapidly, to make the sodium chloride aqueous solution having the biological molecule become the amorphous ice and frozen biological specimen.

Figure 3:
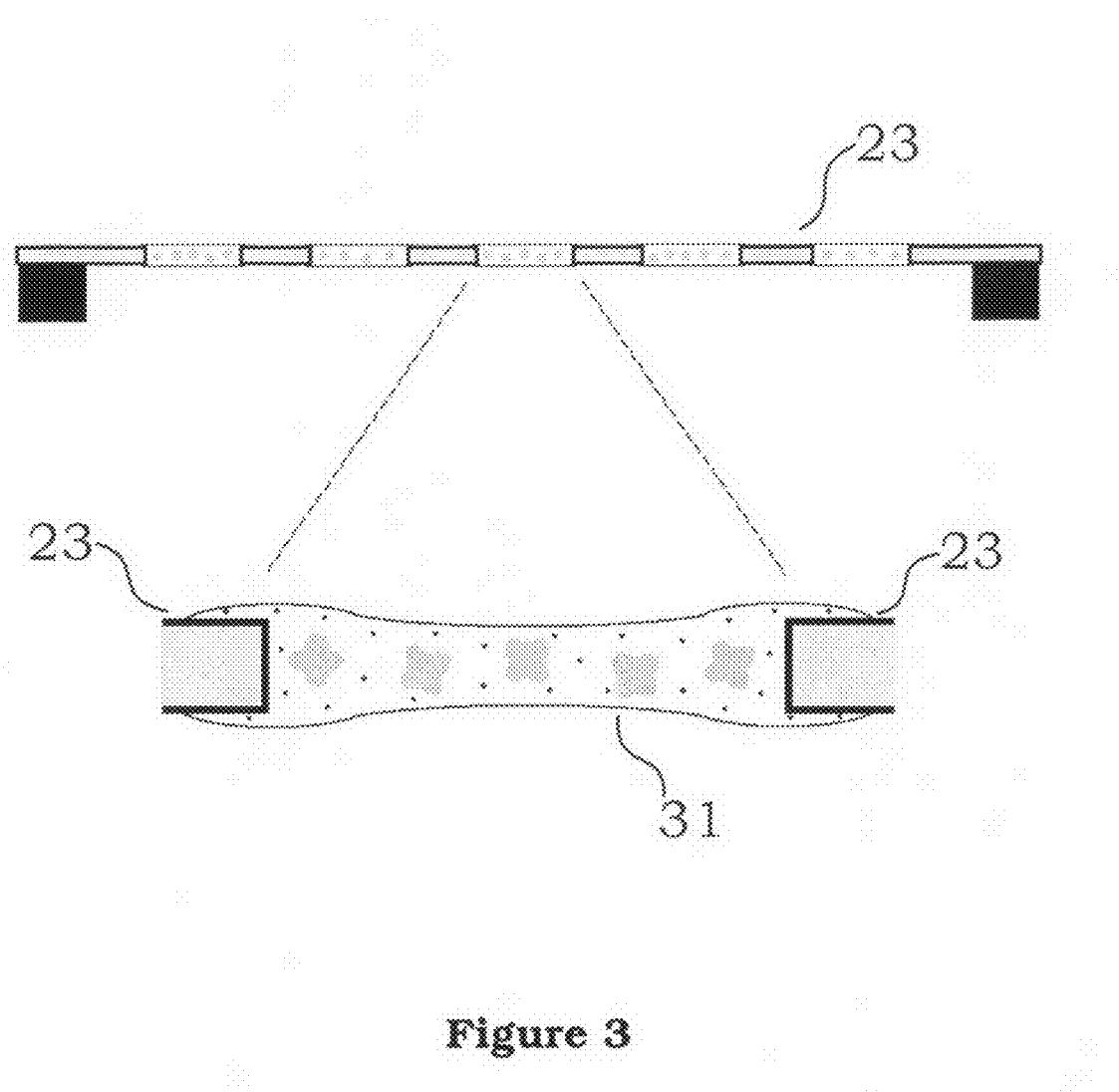
FIG. 3 is the magnified diagram schematically illustrating the cross-section of preferred embodiment of the invention.

As shown in FIG. 3, the magnified diagram is for the cross-section of specimen grid 23. The frozen biological specimen 31 is stored in the specimen grid 23. The specimen grid is a holey carbon film, which is made of the carbon thin film. A gold (Au) film or other metal film of about 5 nm is coated on the both sides of the holey carbon film.

The frozen biological specimen 31 in the specimen grid 23 is transferred and fixed on the specimen holder 15. Now, the specimen holder 15 has to be kept at about 77K. Then, the specimen holder 15 is transferred into the electron microscope.

Then, using power supply 11 to provide suitable current is carried out to charging the frozen biological specimen. After the specimen is charged, the photographing process is conducted by the electron microscope.

Figure 4:
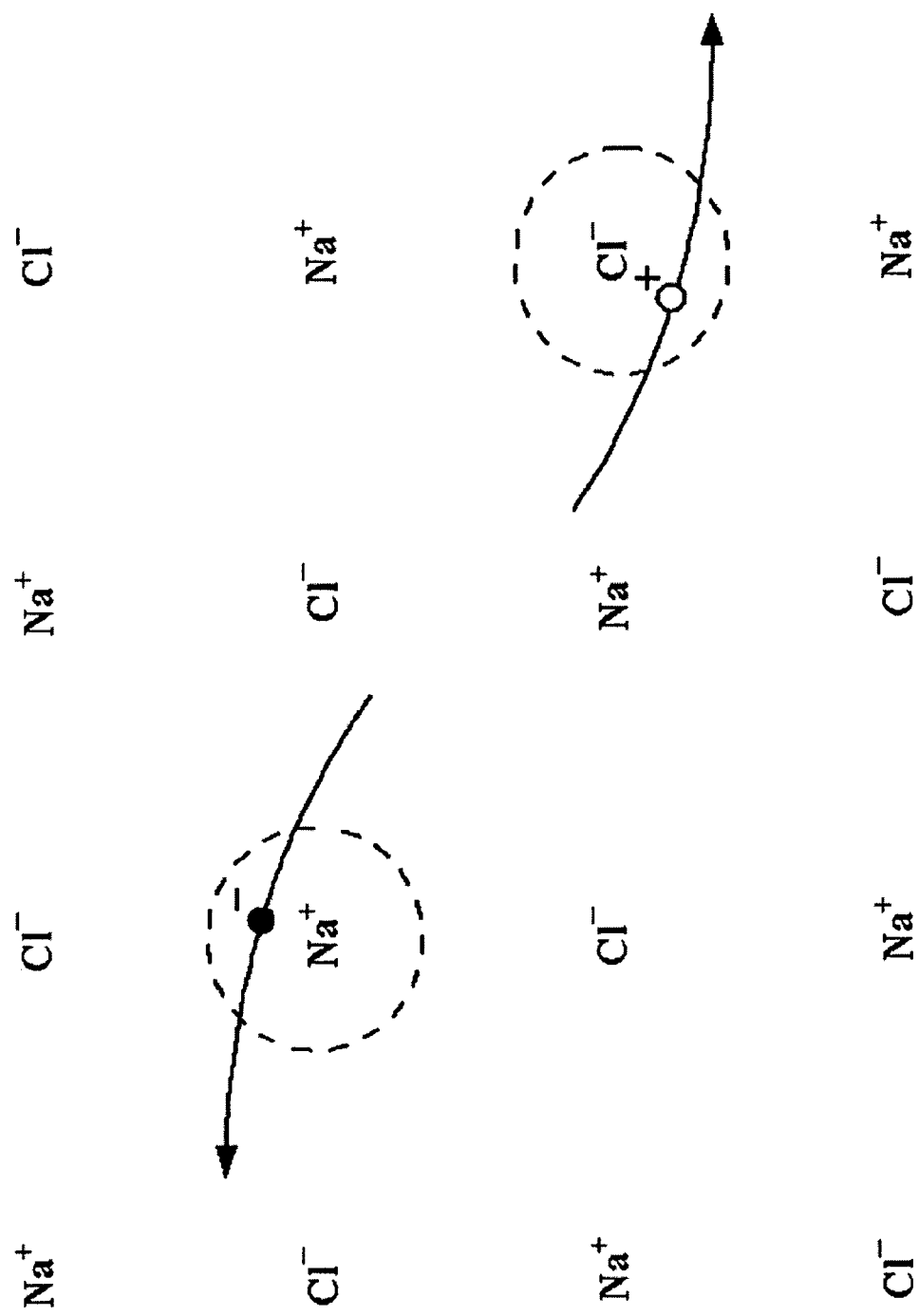
FIG. 4 is the diagram schematically illustrating the electron-hole pair of Na+ and Cl− of the invention.

After the above-mentioned rapid low-temperature freezing procedure, the specimen and aqueous solution will become the vitrified ice like an amorphous frozen liquid. As shown in FIG. 4, the sodium chloride (NaCl) doped amorphous frozen liquid will possess the electron-hole pair of sodium ion (Na+) and chlorine ion (Cl−). In the present invention, after Na+ doped water or amorphous ice is rapidly frozen to the low temperature, the energy gap will be reduced, and make it become a semiconductor with good conductivity.

When the specimen is observed by the electron microscope, if a 4 k×4 k image detector (CCD) is used, the image resolution is about 0.25 Å per pixel at a magnification of 100,000×. Thus it has good resolution to match with atomic model, which can become the bio-molecular microscope with atomic resolution directly.

Figure 5A:
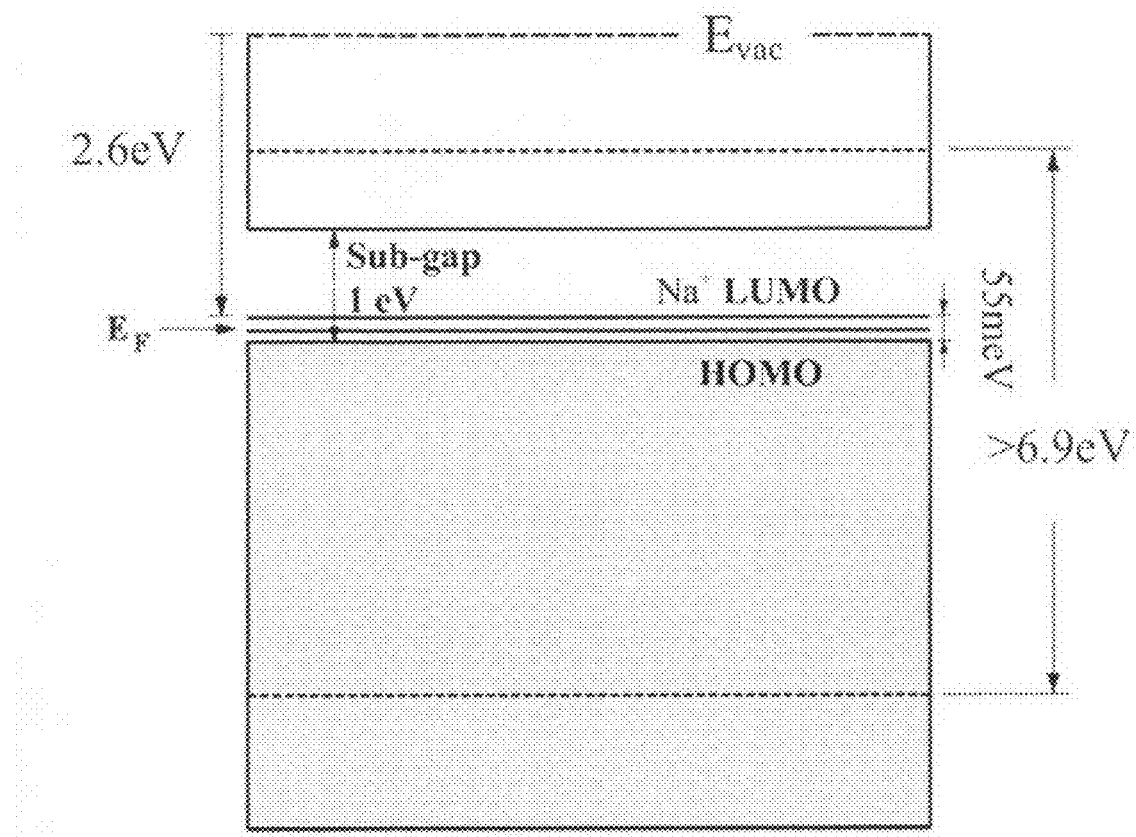
FIG. 5A is the diagram schematically illustrating the energy band of Na+ doped amorphous ice of the invention.

As shown in FIG. 5A, when the water or amorphous ice is doped by small amount of impurity ions at several μM to mM, the frozen specimen will become the doped amorphous organic semiconductor. However, if the concentration of impurity ions is too high (>100 mM), then the resolution of electron microscope will be influenced. In the present invention, the doped ions such as sodium ion and chlorine ion are not heavy metals. The concentration shall be controlled below about 100 mM, to avoid influencing the contrast and resolution of the electron microscope. The thickness of ice embedded specimen shall be controlled below about 100 nm, to avoid influencing the resolution of electron microscope due to the occurrence of multiple electron scattering. As shown in FIG. 5A, again, when the water or amorphous ice is not doped by any impurity ion, its energy gap will be at least 6.9 eV. The energy gap can be reduced to 1 eV due to the interaction between the doped sodium ions and water molecules. The lowest unoccupied molecular orbital (LUMO) of the sodium ions is located very close to the Fermi level ($E_F$) and the highest occupied molecular orbital (HOMO) of doped water, thus the amorphous ice doped by suitable amount of sodium ions will have the same property of semiconductor. The energy level for other ions such hydroxyl ion (OH−), hydrogen ion (H+), and $H^{3+}O$ are located very far away from the Fermi level ($E_F$), thus it is known that the sodium ion is in charge of electron conduction in amorphous ice. In the FIG. 5A, $E_{vac}$ is the energy level at the vacuum.

Figure 5B:
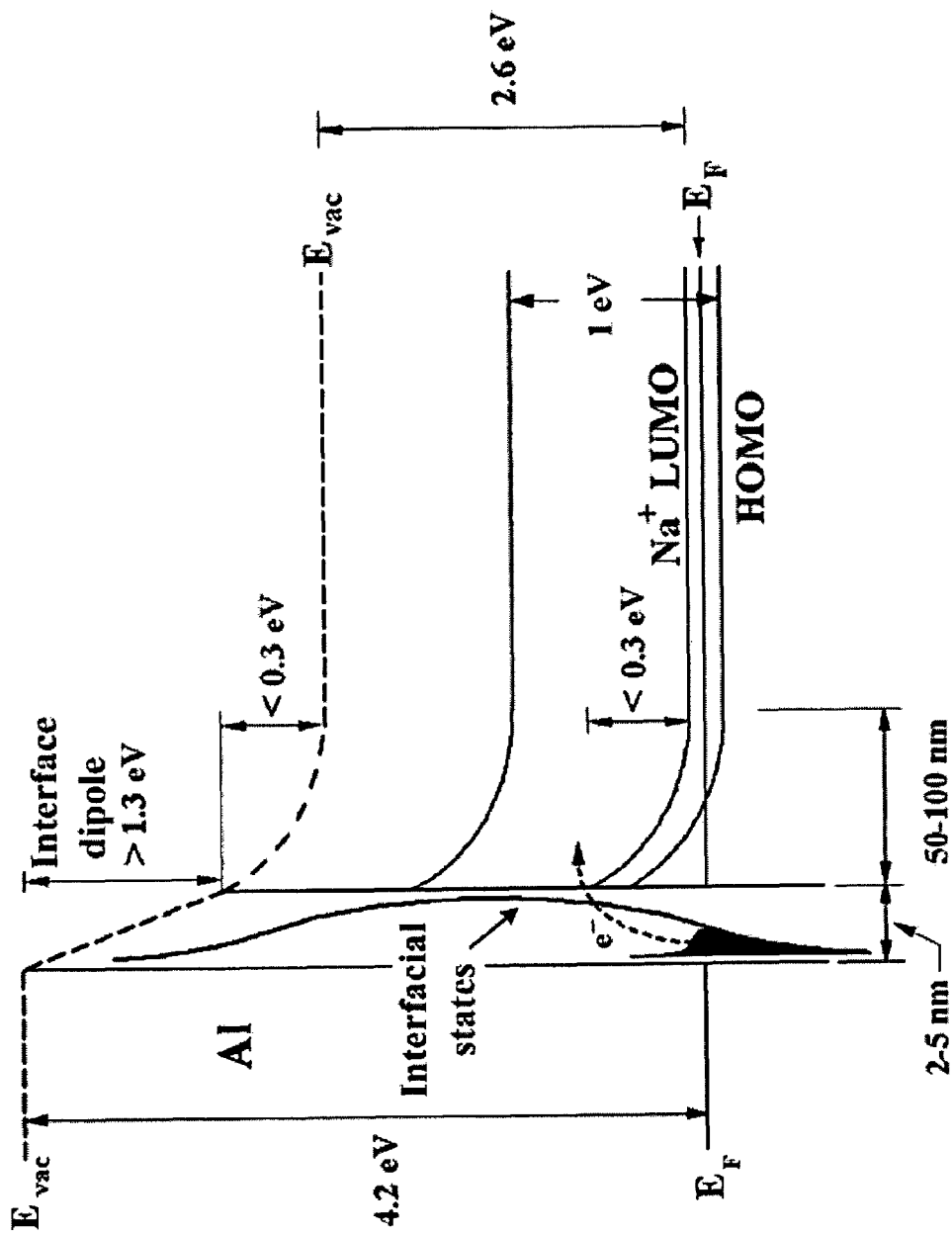
FIG. 5B is the diagram schematically illustrating the energy barrier between Na+ doped amorphous ice and metal of the invention.

In addition, as shown in FIG. 5B, the aluminum metal (Al) is used as the interface in contact with the doped amorphous ice. The work function of Al is 4.2 eV, and the work function of Na+ is 2.6 eV (this value is very close to the Fermi level of Na+ doped amorphous ice). Under thermal equilibrium, the Fermi level at left end and right end shall be level and become equal. The interfacial dipoles exist within a few nanometers (2-5 nm) from the interface of amorphous ice. The interface dipole can greatly reduce the energy barrier at the metal-organic amorphous semiconductor interface (in the case here, the interface dipole at the interface between aluminum metal and Na+ doped amorphous ice is larger than 1.3 eV). Thus the actual energy barrier formed by the upward Na+ LUMO bending at the interface is only about 0.3 eV or smaller. Moreover, when Na+ doped vitrified ice is being charged, the electrons injected from metal electrode can either hop over or tunnel through about 0.3 eV of energy barrier into the doped amorphous ice via the interfacial states at the organic-metal contact interface.

Figure 6:
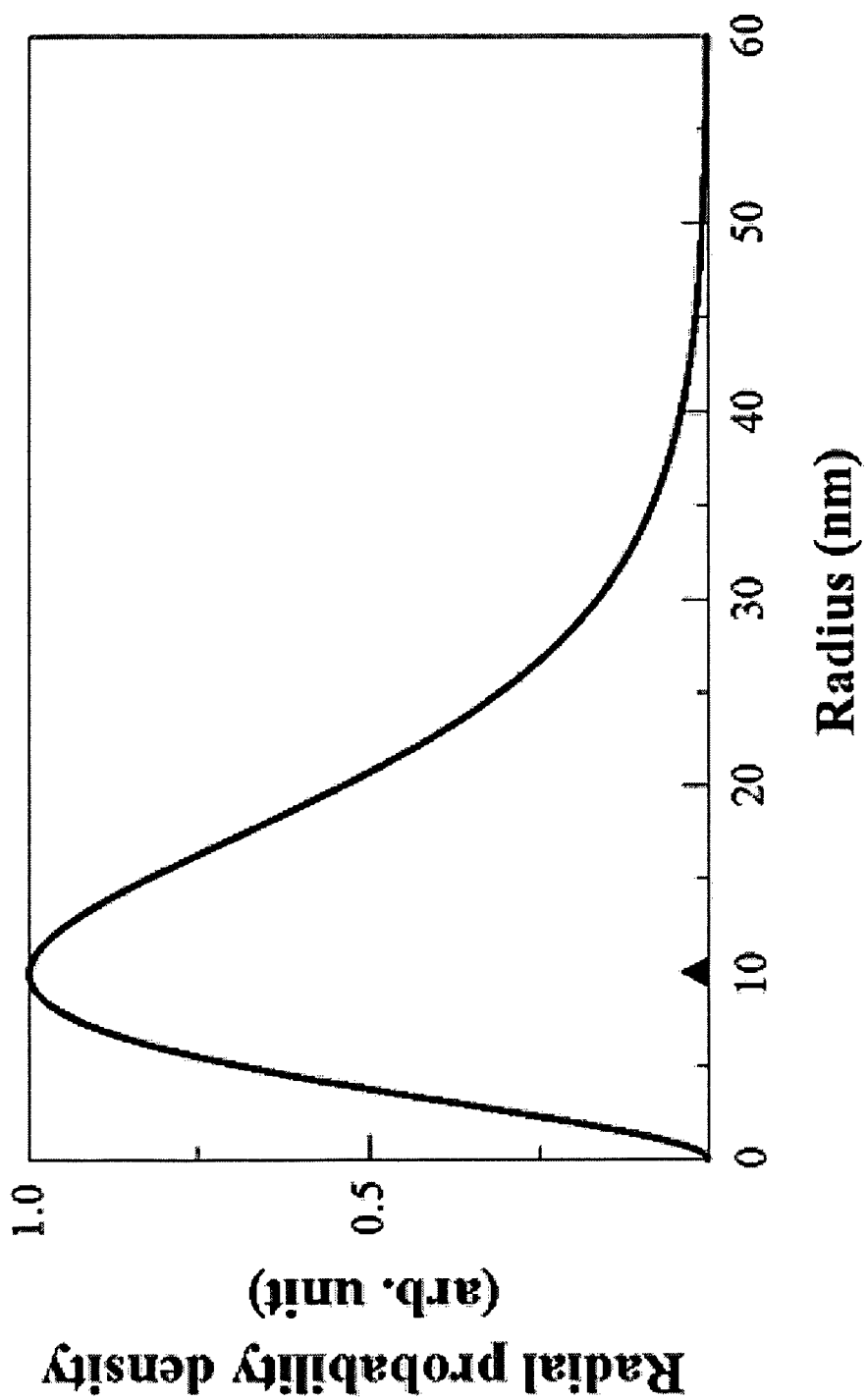
FIG. 6 is the diagram schematically illustrating the radial probability density of the electron wave-function bound to the Na+ center of the invention.

As shown in FIG. 6, the radial probability density of the electron wavefunction bound to the Na+ center is plotted. The radius of the electron wavefunction bound to the center of the Na+ is about 10 nm. If the distance between adjacent Na+ ions is less than about 20 nm (the concentration of Na+ here is about 50 μM), the electron wavefunction will overlap appreciably, so that charged Na+ doped amorphous ice can have a conductivity level comparable to those of metals.

As for the bound energy, when the kinetic energy of electron is larger than the bound energy of ice-embedded Na+ on electron (0.7 meV), the electrons can move freely even at 77K, because the kinetic energy of electron is 6 meV at this temperature, and the mobile electron can be described by the wavefunction in the form of traveling waves. Moreover, there will have appreciable overlap between adjacent electron wavefunction, so that the charged Na+ doped amorphous ice can have a conductivity level comparable to that of metals. Therefore, when the ice-embedded biological sample is damaged by electron beam irradiation, the free mobile electrons in Na+ doped amorphous ice can promptly and continuously supply electrons to ionized atoms and molecular fragments in the frozen sample to scavenge the radiation damage in it. In addition, as shown in FIG. 5B, after the charging process of the present invention, it is almost impossible for the free electron to escape out from the doped amorphous ice. Because the kinetic energy of electron is only $6 \times 10^{-3}$ eV at 77K, which is much smaller than 0.3 eV of energy barrier at the Al metal-amorphous ice interface, thus the traveling electrons can not cross over the energy barrier, hence they can be kept in Na+ doped amorphous ice for a long time. These free electrons stored in ion doped amorphous ice can be distributed evenly in the energy level of the lowest unoccupied molecular orbital (LUMO) of the Na+ ions. If the spin direction of electron is not considered, the number of free electrons stored in the amorphous ice is equal to the number of doped ions.

As shown in FIGS. 7A1, 7A2 and 7A3, the damaged molecular fragment of frozen hydrated DNA caused by electron beam irradiation is depicted schematically. When there are no ions doped in the amorphous ice, the reparation by electron and hole transfer can only occur in small clusters of DNA (the cluster is shown by the dashed line; the diameter of cluster is about 4-5 nm). Thus the radicals and ionized molecular fragments damaged by electron beam irradiation can not be repaired completely. However as shown in FIGS. 7B1, 7B2 and 7B3, if the amorphous ice is doped by suitable amount of ions (such as Na+ and Cl− etc.), when DNA molecule is damaged by electron radiation, the distant electron and hole can promptly jump into the clusters via the doped Na+ and Cl− ions outside the clusters to repair the ionized atoms and molecular fragments damaged by electron radiation, thus, as to scavenge the free radicals or the ionized molecular fragments that occur during electron beam irradiation.

Figure 8:
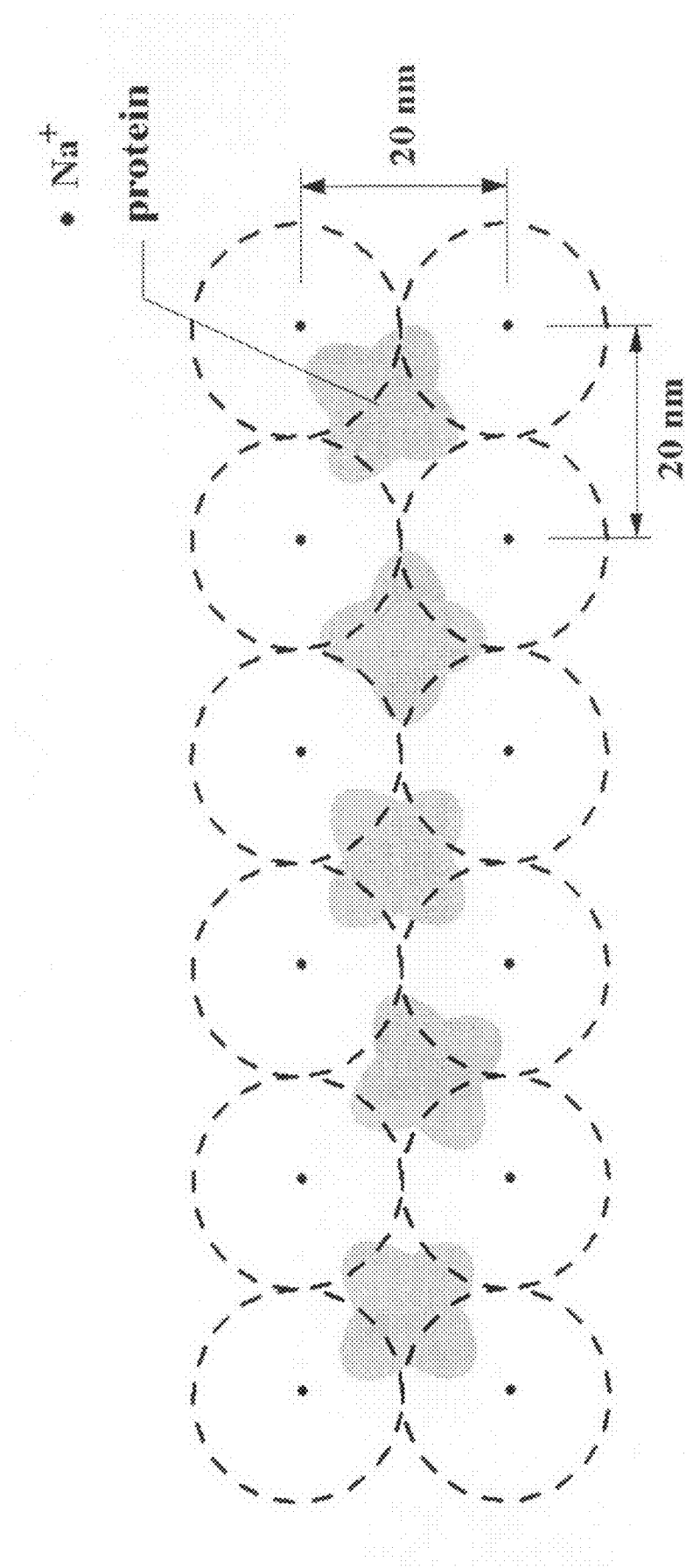
FIG. 8 is the diagram schematically illustrating the radius range of electron wave-function around each sodium ion will overlap the ice-embedded biological molecule (e.g. protein) of the invention.

Thus, as shown in FIG. 8, when the average distance among sodium ions is controlled below or equal to 20 nm (the concentration of Na+ is about 50 μm here), the radius range (shown by the dashed circle in the FIG. 8) of electron wavefunction around each sodium ion will overlap the ice-embedded biological molecule such as protein in the case here. Now, the protein is looked like to be embedded in a conducting environment. When the protein embedded in the amorphous ice is damaged by electron radiation, the free electrons in Na+ doped amorphous ice can promptly tunnel into protein molecule to repair the damaged molecular fragments occurring under electron beam irradiation. The electron or hole entering protein molecule can promptly tunnel or diffusively hop through the damaged protein molecule to repair the ionized atoms and molecular fragments (frozen free radicals) in it. Thus, the free electrons stored in ion doped amorphous ice by charging can repair the radiation damage caused by electron beam irradiation at any time. Thus, the radiation damage caused by electron beam irradiation can be reduced greatly or even eliminated. In other words, the present invention increases the electron dosage tolerance of the biological material greatly and thus raises the resolution of electron microscope to the atomic level for the biological material.

In the present invention, when the impurity ions are doped to certain concentration, the frozen specimen will become the conductor. The free electrons stored in the doped frozen specimen can promptly supply electrons to ionized molecular fragments in the frozen sample and efficiently repair the radiation damage caused by electron radiation at any time, to scavenge the radiation damage of the biological molecules occurring under electron beam irradiation. In the preferred embodiment of the present invention, the doping ions used include Na+, Cl−, K+, Br−, I−, $Mg^{2+}$, $Ca^{2+}$ etc.; or charged amino acid; or other charged molecules; or the other molecules that possess some certain level electron-affinity; or the donor atom or molecule which can provide extra one electron; or the acceptor atom or molecule which can provide extra one hole.

The major feature of the invention is to charge the biological specimen and freeze the specimen at low temperature. The ice around the biological sample is also doped, so that after charging the doped ice surrounding the sample has a conductivity level comparable to that of conductor. Thus, the sample can be embedded by the doped and charged ice obtaining the property of conductor. Thus, the free electrons stored in ion doped amorphous ice by charging can promptly return electrons to the ionized molecular fragments and repair the radiation damage under electron beam irradiation at any time, to increase the electron radiation tolerance of the biological molecules greatly. It will be advantageous to observe the biological specimen by the electron microscope.

It is understood that various other modifications will be apparent and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A cryo-charging specimen holder for an electron microscope, comprising:
    a power supply connected to a resistor via an electrical wire and connected to a specimen holder through a specimen rod; and
    a vacuum adiabatic flask having an inner pot, wherein a vacuum space being located between the vacuum adiabatic flask and the inner pot, a liquid cooling medium being filled in the inner spot, and the inner pot is connected to the specimen rod.

2. The holder according to claim 1, wherein the specimen holder comprises a specimen grid.

3. The holder according to claim 1, wherein the specimen holder comprises a hexring screw.

4. The holder according to claim 1, wherein the specimen holder comprises a Teflon washer.

5. The holder according to claim 1, wherein the specimen holder comprises a groove for electrical wire.

6. A method for using a cryo-charging specimen holder of an electron microscope, comprising:
    processing a vacuum treatment;
    processing low-temperature treatment, the low temperature being transferred to a specimen holder from a specimen rod;
    installing a pretreated specimen grid into the specimen holder, and a biological specimen been loaded in the pretreated specimen grid;
    installing the cryo-charging specimen holder of an electron microscope in the electron microscope;
    using a power supply for providing a suitable current to charge a biological specimen through a resistor connected to electrical wires and
    observing the biological specimen by the electron microscope.

7. The method according to claim 6, wherein the specimen grid comprises Na+ aqueous solution.

8. The method according to claim 7, wherein the concentration of Na+ aqueous solution is between 1 $\mu$M to 100 mM.

9. A method for treating a cryo-charging specimen for an electron microscope, comprising:
    adding a biological material in a liquid solution having specific property for forming a biological specimen;
    processing a frozen treatment; and
    processing a charging treatment by using a power supply to provide a current.

10. The method according to claim 9, wherein the liquid solution comprises Na+ aqueous solution.

11. The method according to claim 10, wherein the concentration of Na+ aqueous solution is between 1 $\mu$M to 100 mM.

12. The method according to claim 9, wherein the liquid solution having specific property comprises a conduction channel close to the Fermi level.

* * * * *